United States Patent
Feygin (10) Patent No.: US 6,563,117 B2
(45) Date of Patent: May 13, 2003

(54) ARTICLE COMPRISING IR-REFLECTIVE MULTI-WELL PLATES

(76) Inventor: Ilya Feygin, 853 Hillside Ave., Mountainside, NJ (US) 07092

(*) Notice: Subject to any disclaimer, the term of this patent is extended or adjusted under 35 U.S.C. 154(b) by 0 days.

(21) Appl. No.: 09/872,211

(22) Filed: Jun. 2, 2001

(65) Prior Publication Data

US 2002/0179835 A1 Dec. 5, 2002

(51) Int. Cl.[7] .......................... G01N 21/35; G12M 1/00
(52) U.S. Cl. .................. 250/332; 250/339.02; 422/102; 435/305.2
(58) Field of Search ............................ 250/332, 339.02, 250/461.2, 458.1; 422/102; 435/305.2, 305.3, 305.4

(56) References Cited

U.S. PATENT DOCUMENTS

| | | | | |
|---|---|---|---|---|
| 5,002,889 A | * | 3/1991 | Klein | ........................... 702/21 |
| 5,846,708 A | * | 12/1998 | Hollis et al. | ................. 257/253 |
| 6,030,917 A | * | 2/2000 | Weinberg et al. | .............. 435/4 |
| 6,171,780 B1 | * | 1/2001 | Pham et al. | ................. 422/102 |
| 6,214,293 B1 | * | 4/2001 | Pantoliano et al. | ....... 250/458.1 |
| 6,320,996 B1 | * | 11/2001 | Scobey et al. | .............. 359/128 |
| 2002/0032531 A1 | * | 3/2002 | Mansky et al. | ................ 702/21 |

FOREIGN PATENT DOCUMENTS

WO    WO 9815813 A1 *  4/1998   .......... G01N/21/35

* cited by examiner

Primary Examiner—Constantine Hannaher
Assistant Examiner—Albert Gagliardi
(74) Attorney, Agent, or Firm—DeMont & Breyer, LLC

(57) ABSTRACT

An article including a multi-well plate that has an infrared radiation ("IR") reflective coating disposed over the surface of the wells. In some embodiments, the wells have a parabolic or near parabolic shape. In additional embodiments, the wells, which have a parabolic or near parabolic shape, are truncated at or near a focal plane of the well. In some further embodiments, the wells have a hemispheric shape or a truncated hemispheric shape. IR imaging systems that incorporate the multi-well plates described herein exhibit improved sensitivity and signal-to-noise ratio.

26 Claims, 8 Drawing Sheets

ARTICLE COMPRISING IR-REFLECTIVE MULTI-WELL PLATES

FIELD OF THE INVENTION

The present invention relates generally to multi-well plates and to their use in conjunction with infrared spectrum imaging systems.

BACKGROUND OF THE INVENTION

In assay screening, a large number of cellular events (e.g., calcium flux, etc.), physiological events and/or molecular events (e.g., chemical reactions, etc.) are monitored and analyzed. These events, hereinafter referred to as "target events," are often carried out in multi-well (e.g., micro-titer) plates. As the name "multi-well" implies, these plates contain a multiplicity of wells (96-well, 384-well, 1536-well plates are typical) that are organized in a two-dimensional array. The wells are quite small, having a diameter that is typically in a range of about 1 millimeter to about 6 millimeters as a function of the number of wells in the plate.

Due to the large number of events taking place in the wells, time-consuming methods that directly examine each well (e.g., microscopic examination, etc.) are unsuitable for data acquisition. To screen such a large number of events, a "snap shot" of the whole plate is advantageously taken using various imaging techniques.

Perhaps the most common imaging techniques are those that image visible spectrum light, such as fluorescence imaging and luminescence imaging. In the former process, when an event of interest (e.g., a cellular event, physiological process, chemical reaction, etc.) occurs, a detection reagent emits light (i.e., fluoresces) when excited by an appropriate excitation source (e.g., ultraviolet light). The emitted light, which provides qualitative and/or quantitative information about the event, is captured and converted to electrical signals using, for example, a charge coupled device ("CCD"). The CCD comprises an array of thousands of cells that are capable of receiving light from multiple wells at the same time. The signals are analyzed, via suitable software, to recover information concerning the event. Luminescent imaging (chemi- or bio-) is similar to fluorescence imaging, except that excitation light is not required.

Area or array-type fluorescent imaging devices are very complex and, hence, very expensive (c.a., $100,000 to $400,000). These imaging devices typically include an excitation light source, complicated optics, filters, a CCD, a cooler for the CCD, a control unit, software, positioners, and other elements. While an excitation light source is not required for luminescence imaging, many of the luminescent reactions are so dim that a highly optimized imaging system, including the most sensitive form of cooled CCD camera and very efficient lenses, are required.

In addition to the high cost of such imagers, fluorescence and luminescence imaging is complicated by the requirement of a suitable detector reagent. While specific detector reagents have been developed for various applications, there are no universally applicable reagents.

Consequently, a less costly and less complicated alternative to visible spectrum (i.e., fluorescence and luminescence) imaging is desirable. One possible alternative is thermal or infrared imaging, wherein a change in energy that accompanies every chemical reaction and physiological process is monitored to obtain useful information. The energy change is observed as a temperature change within the wells of the multi-well plate.

Temperature changes that are being monitored are often quite small. In fact, temperature changes due to reaction and physiological processes can be significantly smaller than temperature changes due to incidental processes, such as evaporation. Furthermore, infrared radiation that is emitted from nearby objects can propagate into the wells of the multi-well plate and be imaged by the detector, swamping any temperature changes that might have occurred due to reaction, or at least introduce error into the measurements.

Consequently, there is a need for a way to improve the sensitivity or otherwise increase the signal-to-noise ratio of infrared imaging processes.

SUMMARY OF THE INVENTION

The problems described above related to infrared imaging are ameliorated by a multi-well plate that includes an infrared radiation ("IR") reflective coating over the surface of the wells, in accordance with the illustrative embodiment of the present invention. In some embodiments, the reflective coating comprises a layer of a metal, such as gold, copper or the like.

The reflective coating provides at least two benefits. One benefit is that more of the IR radiation that is generated by target events is reflected toward the IR detector. A second benefit is that, with an appropriately deep well, stray IR that is introduced into a well from external sources is substantially totally internally reflected by the IR reflective coating. Consequently, such stray IR is not imaged, does not appear as noise and does not interfere with the measurement of temperature changes that are due to the target events being monitored.

In some multi-well plates described herein, the wells have a parabolic or near parabolic shape. Substantially all of the IR that is emitted at or near the focal point of such wells is reflected out of the mouth of the well (i.e., toward the IR detector) rather than dissipating into the plate. The parabolic shape of the well collimates IR emitted from the focal point such that path of radiation out of the well is normal to the surface of the multi-well plate and normal to the IR detector. Consequently, parabolic-shaped wells reduce the incidence of "spillover" wherein IR is detected by a neighboring detector element (or group of detector elements) that are "assigned" to detect the IR emitted from neighboring wells.

Improved infrared imaging systems in accordance with the illustrative embodiment of the present invention incorporate the multi-well plates described herein. And, as a consequence, some of the IR imaging systems described herein exhibit a higher signal-to-noise ratio than some prior art IR imaging systems.

One infrared imaging system described herein comprises a multi-well plate as described above, a multi-well plate holder for supporting the multi-well plate, an isothermal chamber that receives the multi-well plate holder and the multi-well plate, an infrared camera that is focused on the multi-well plate and signal processing electronics that are electrically connected to the infrared camera and that are operable to receive a signal that is generated thereby.

A second infrared imaging system described herein comprises a multi-well plate as described above, and an IR detector in the form of a focal plane array that is disposed in parallel, opposed and aligned relation therewith. In some variations, the IR detector and the multi-well plate are separated by a space that is about one millimeter or less.

A third infrared imaging system described herein comprises a multi-well plate as described above and a detector plate. The detector plate comprises a plurality of wells having a parabolic shape, an IR-reflective coating disposed on the wells, and a sensor element that is disposed at a focal point within the wells. In some variations, the multi-well plate is separated from the detector plate by a space that is about one millimeter or less.

A fourth infrared imaging system described herein comprises a multi-well plate and a reflector that abut one another in opposed and aligned relation. The wells in the multi-well plate have an IR reflective coating and a hemispherical or truncated hemispherical shape. In some embodiments, the reflector comprises a plurality of wells, each having a hemispherical shape and having an IR reflective coating. When the multi-well plate and the reflector are brought together, wells aligned, each pair of aligned wells forms a substantially spherical enclosure. Each spherical enclosure is provided with a "radiation-transparent window" through which emitted IR escapes from the enclosure. The radiation-transparent window is the only location at which emitted IR can escape from the enclosure. The radiation-transparent window leads to an IR sensor element.

A method in accordance with the illustrative embodiment of the present invention comprises: emitting IR near a focal plane, receiving the emitted IR at a first surface and reflecting it therefrom in a direction that is substantially perpendicular to the focal plane, receiving the reflected IR at a second surface and reflecting it therefrom to a focal point and detecting said infrared radiation at said focal point.

DETAILED DESCRIPTION

The terms listed below are given the following specific definitions for the purposes of this specification.

"Infrared Spectrum Radiation" means radiation having a wavelength within a range of about 780 nanometers to about 1 millimeter. The infrared region of the electromagnetic spectrum is sometimes broken down into three sub-regions. These sub-regions include: (1) the "near-infrared" region spanning wavelengths of about 0.7 to 1.5 microns; (2) the "intermediate-infrared" region including wavelengths of about 1.5 to 20 microns; and (3) the "far-infrared" region covering a range of wavelengths from about 20 to 1000 microns.

"Low thermal conductivity" means a thermal conductivity of about 1 B.t.u./(sq.ft.)(hr.)(° F./in.) or less.

"Reagents" means cellular material, non-cellular material and/or chemicals. Generally, the term "reagent" means anything that is a reactant, solvent or otherwise participates in target events.

"Specimen plate" means a plate on which reagent(s) are disposed. The term "specimen plate" includes multi-well (e.g., micro-titer) plates. Such plates have a plurality of wells (96-well, 384-well, 1536-wells are typical) that are organized in a two dimensional array. The term "specimen plate" also refers to a glass or plastic slide that does not have wells, upon which reagents are deposited in large two-dimensional arrays.

"Target events" means cellular, physiological and/or molecular events, such as, for example, calcium flux, chemical reactions, etc.

"Visible spectrum radiation" means radiation having a wavelength in the visible range, which is in a range of about 390 nanometers to about 780 nanometers.

Other terms that are to be given a specific definition for the purposes of this specification are identified later herein in bold font and are set-off by quotation marks.

In accordance with the illustrative embodiment of the present invention, improved IR imaging systems incorporate modified multi-well plates that are described herein. The modified multi-well plates possess:

in some variations, an ability to internally reflect stray infrared radiation;

in some variations, an ability to reflect more emitted infrared radiation than conventional multi-well plates; and in some variations, an ability to collimate emitted infrared radiation.

As a consequence of any one of these attributes, multi-well plates described herein increase the signal-to-noise ratio of IR imaging systems. Before addressing the specifics of such improved IR imaging systems, multi-well plates in accordance with the illustrative embodiment of the present invention are described.

Figure 1:
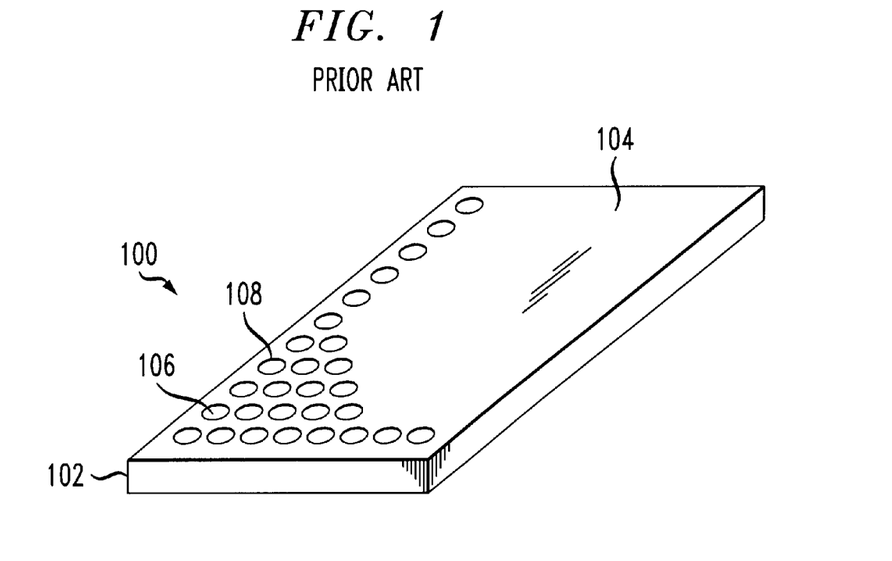
FIG. 1 depicts a conventional multi-well plate.

FIG. 1 depicts conventional multi-well plate 100. The multi-well plate includes base 102 having upper surface 104. A plurality of wells 106 are disposed in base region 102. Mouth 108 of each well is substantially co-planar with upper surface 104.

Multi-well plate 100 is a 96-well plate, which is typically implemented as an 8×12 array of wells 106. The overall thickness of multi-well plate 100 is about 15 millimeters. While the dimensions of wells 106 vary somewhat from manufacturer to manufacturer, wells 106 in a 96-well plate typically have a diameter (at mouth 108) that is about 5–6 millimeters and a depth that is about 9–10 millimeters. The wells in a 384-well plate typically have a diameter of about 3–4 millimeters, and the wells in a 1536-well plate have a diameter of about 1–2 millimeters. The wells in a conventional multi-well plate, such as plate 100, can have any of a variety of shapes or profiles, including, for example, flat, hemispherical, v-bottom, square, etc.

Figure 2:
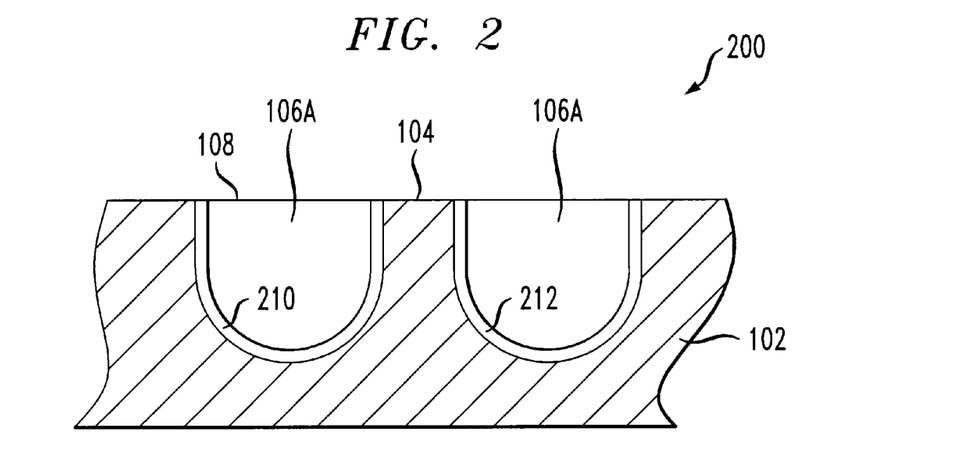
FIG. 2 depicts a multi-well plate in accordance with the illustrative embodiment of the present invention.

FIG. 2 depicts, via a partial, cross-sectional view, multi-well plate 200 in accordance with the illustrative embodiment of the present invention. A coating or layer 212 is disposed on surface 210 of approximately hemispheric-shaped well 106A. Well 106A is actually deeper than it is wide, but the curvature of the well approximates a hemisphere. Coating 212 comprises a material that reflects IR, such as, without limitation, gold or polished copper. Coating 212 should be sufficiently thick to prevent penetration of IR into base 102; to that end, coating 212 should be at least about 1000 angstroms thick. Coating 212 should not be applied to upper surface 104. Coating 212 can be applied by Epner Technologies, Brooklyn, N.Y. or others. Base 102 is made of a material that does not substantially conduct heat—that is, has low thermal conductivity—such as plastics and rigid foams and the like.

Figure 3:
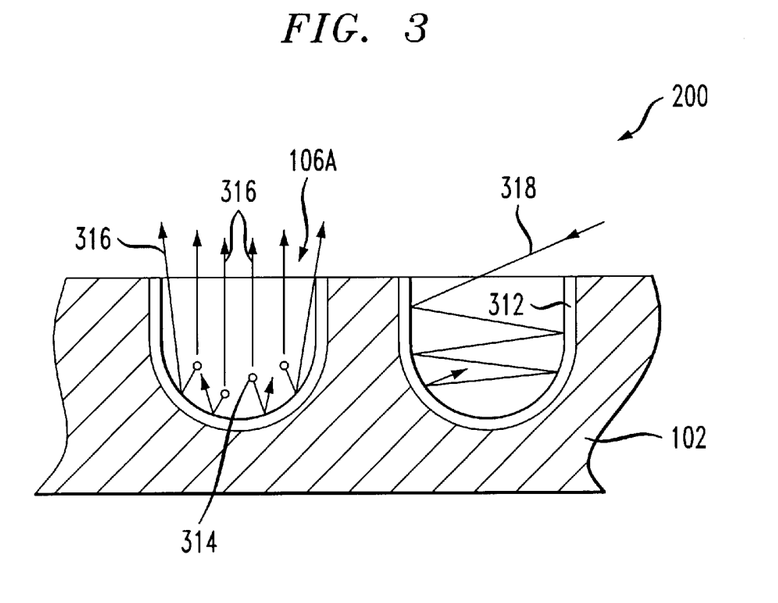
FIG. 3 depicts the suppression of stray IR via total internal reflection within the multi-well plate of FIG. 2.

FIG. 3 depicts infrared radiation, illustrated via rays 316, being emitted due to target events that take place in conjunction with reagents 314 that are present in well 106A. IR-reflective coating layer 312 increases the amount of such emitted IR 316 that escapes the well relative to the amount escaping from a well that is not so coated, such as well 106 of conventional multi-well plate 100. IR-reflective coating layer 312 thereby improves the sensitivity and the signal-to-noise ratio of IR imaging systems described herein.

Furthermore, IR reflective coating layer 312 substantially prevents stray IR (i.e., infrared radiation that enters the well from external sources) from escaping well 106A. Specifically, stray IR is internally reflected by IR-reflective coating layer 312 such that much of such stray IR, illustrated via ray 318 in FIG. 3, is not re-radiated from well 106A. To the extent that stray IR is not re-radiated, such stray IR is not imaged by an infrared detector that is focused on or otherwise receives IR from well 106A. Since IR-reflective coating 312 substantially reduces the amount of re-radiated stray IR, an IR imaging system that receives IR from well 106A is subject to less noise. This reduction in re-radiated stray IR also contributes to an increase in signal-to-noise ratio for IR imaging systems that use multi-well plate 200 described herein.

Figure 4:
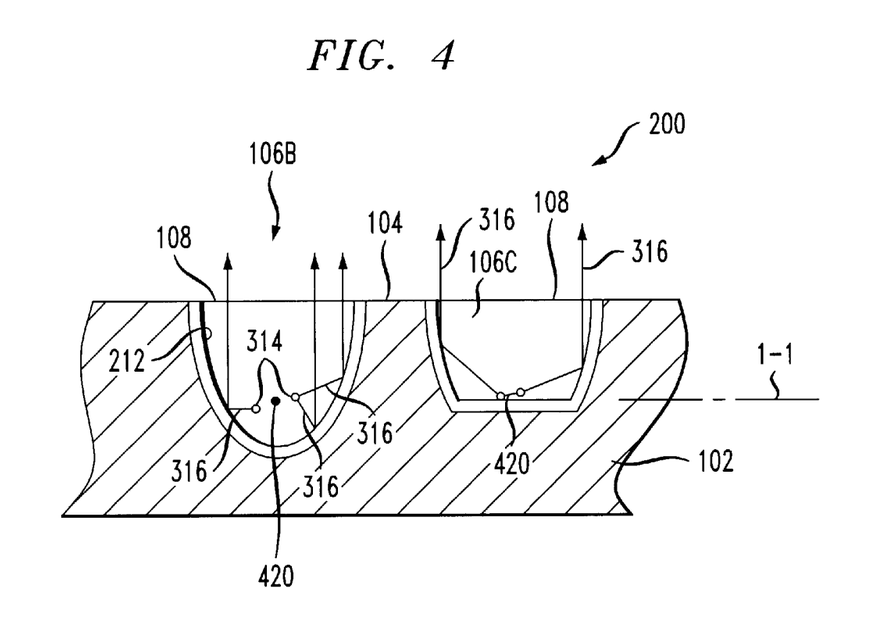
FIG. 4 depicts IR radiation being collimated by the parabolic shape of the multi-well plate of FIG. 2.

In a variation depicted in FIG. 4, some multi-well plates in accordance with the illustrative embodiment of the present invention contain wells 106B or wells 106C. Wells 106B and wells 106C have a parabolic or near-parabolic contour. Well 106B exhibits a full parabolic (or near-parabolic) contour while well 106C is truncated at the focal plane 1—1. For convenience, wells 106B and wells 106C are shown together in a single multi-well plate in FIG. 4. It should be understood that in actual practice, all wells in a multi-well plate are usually of the same shape and size such that a multi-well plate would contain one or the other but not both types of wells shown in FIG. 4.

As a consequence of these parabolic shaped wells, substantially all IR 316 that is emitted from a region near focal point 420 of each well and that strikes IR reflective layer 212 is reflected therefrom along a path that is substantially normal to upper surface 104 of multi-well plate 200. The truncated bottom of well 106C helps to ensure that the reagents are positioned close to focal point 420. Parabolic-shaped wells 106B and 106C function, therefore, as a collimator of emitted IR 316, thereby increasing the amount of IR reaching an IR detector. This also contributes to an increase in the sensitivity of IR imaging systems described herein.

IR imaging systems in accordance with the illustrative embodiment of the present invention, which incorporate multi-well plate 200, are now described. These imaging systems are capable of monitoring target events based on accompanying temperature changes using infrared detectors.

The multi-well plates described herein are capable of reflecting radiation spanning the entire infrared region of the spectrum, although the usable sensitivity of quantum effect infrared radiation detectors that are typically used in conjunction with infrared imaging systems is primarily limited to the intermediate-infrared region.

Figure 5:
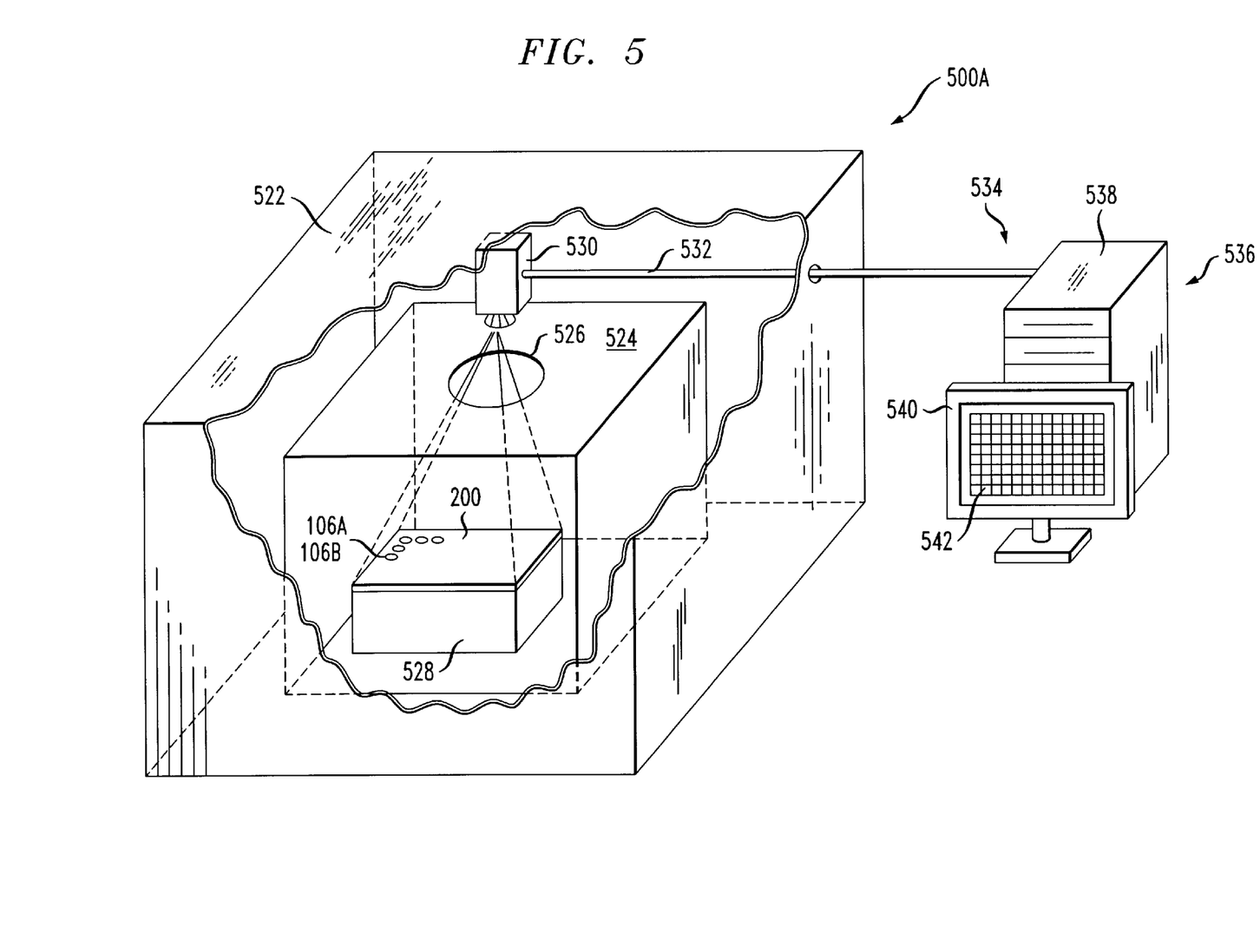
FIG. 5 depicts a first variation of an infrared imaging system in accordance with the illustrative embodiment of the present invention.

A first variation of an IR imaging system in accordance with the illustrative embodiment of the present invention is depicted in FIG. 5. IR imaging system 500A depicted in FIG. 5 is an improvement upon the IR infrared imaging system that is described in published PCT application WO 99/60630, which is incorporated herein by reference. IR imaging system 500A comprises optional culture incubator 522, isothermal chamber 524, multi-well plate holder 528, multi-well plate 200, infrared camera 530, imaging data transfer line 532 and signal processing electronics 534, inter-related as shown.

Multi-well plate 200 is advantageously disposed within isothermal chamber 524. Multi-well plate 200, which has been previously described, has a plurality of wells 106A, 106B or 106C that include IR reflective coating 212 (see FIGS. 2 and 4). In use, wells 106A, 106B or 106C contain reagents that are monitored by IR camera 530 for the occurrence of target events. Multi-well plate 200 is supported by multi-well plate holder 528. For some applications, isothermal chamber 524 and IR camera 530 are advantageously contained within culture incubator 522.

IR camera 530 is capable of simultaneously imaging, through IR-transparent window 526, IR emissions from all wells 106A, 106B or 106C in multi-well plate 200 to a resolution of about 0.02° C. When exposed to IR, IR sensor elements (not shown) that are located within IR camera 530 generate electrical signals indicative of the received IR. IR camera design and manufacture is well understood by those skilled in the art and will not be addressed in this specification. See, P. Finney, "Quantum Effect Infrared Sensing," SENSORS, pp. 32+, (December 1995), incorporated by reference herein. IR cameras are commercially available from a variety of sources, including, for example, Sensors, Inc. of Princeton, N.J.

Electrical signals generated by the IR sensor elements (or electrical signals derived from those signals) are delivered, via imaging data transfer line 532, to signal processing electronics 534. Signal processing electronics comprise an analog-to-digital converter (not shown) and a data processing system 536. Data processing system 536 comprises processor/data storage device 538, display device 540 and various other conventional input and output elements (not shown), such as machine interfaces, a keyboard and the like. The processor is capable of: controlling the operation of IR camera 530, receiving imaging data (after analog-to-digital conversion), storing data in and retrieving data from the data storage device, executing programs (e.g., imaging data-analysis software, etc.) and outputting data to display device 540. Imaging data-analysis software is advantageously capable of generating a representation 542 of multi-well plate 200 that displays the temperature profile within each well 106A, 106B or 106C via a palette of colors.

IR camera 530 is relatively distant from multi-well plate 200 (6 centimeters according to PCT application WO 99/60630). As such, the performance of IR imaging system 500A benefits from the IR reflective wells of multi-well plate 200, which increase the system's signal-to-noise ratio and sensitivity relative to the otherwise identical system disclosed in WO 99/60630.

Figure 6:
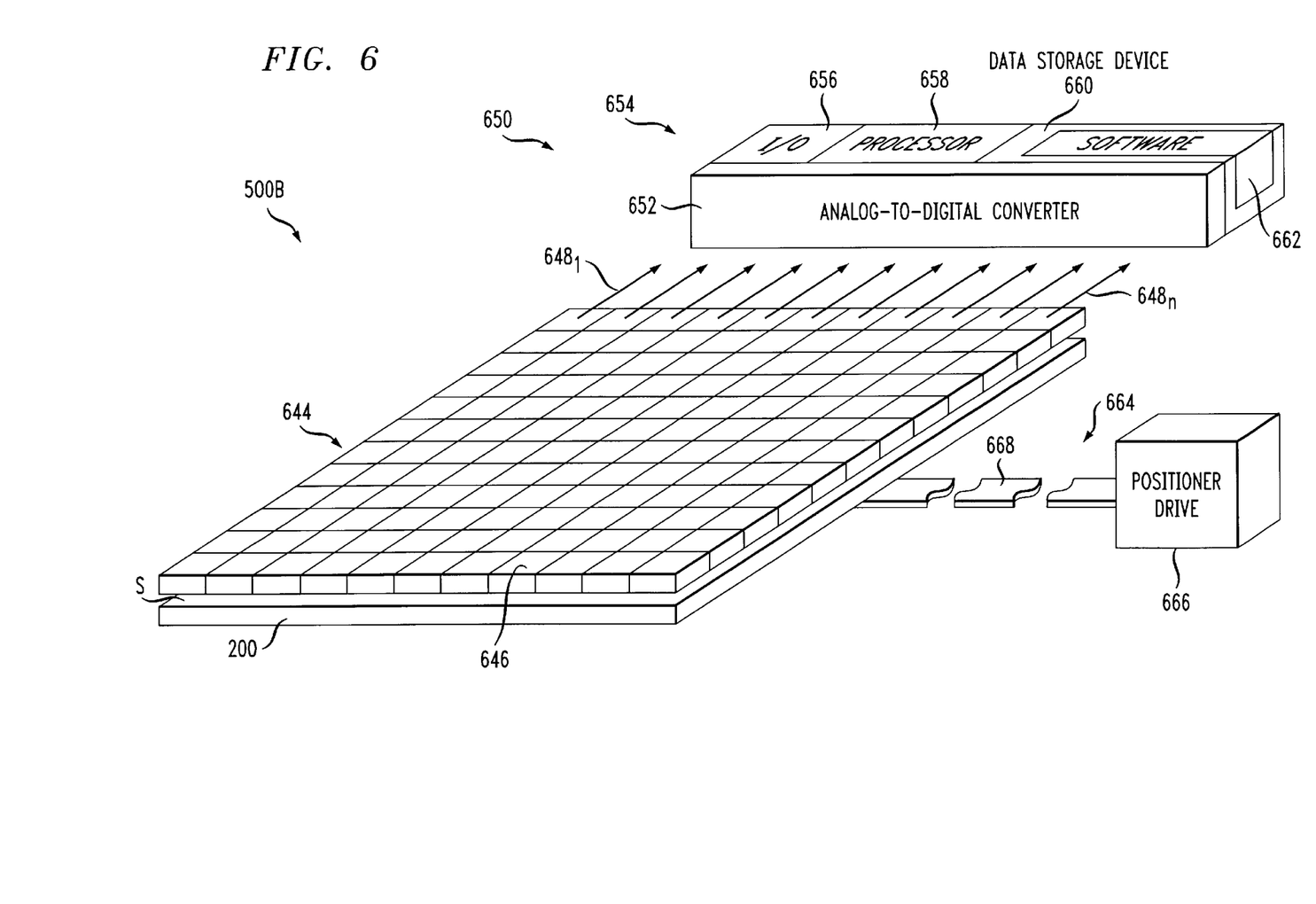
FIG. 6 depicts a second variation of an infrared imaging system in accordance with the illustrative embodiment of the present invention.

A second variation of an IR imaging system in accordance with the illustrative embodiment of the present invention is depicted in FIG. 6. IR imaging system 500B depicted in FIG. 6 is based on an IR infrared imaging system that is described in "Method and Apparatus for Infrared Spectrum Imaging," filed on Jun. 2, 2001 as U.S. patent application No. 09/872,210, which is incorporated herein by reference. IR imaging system 500B comprises multi-well plate 200, infrared detector 644, signal processing electronics 650 and positioner 664, inter-related as shown.

IR detector 644 is advantageously implemented as a focal plane array, well known to those skilled in the art. A focal plane array comprises a regularly organized grouping of thousands of sensor elements 646. A typical array might comprise, e.g., 244 rows, each having 320 sensor elements, for a total of 78,080 sensor elements. Such arrays are advantageously positioned adjacent to one another in order to create a detector capable of covering an area that is size of multi-well plate 200 (e.g., 3 inches by five inches).

IR detector 644 comprises any one of a variety of suitable materials as a function of application specifics. Examples of such materials include (1) lead salts, such as PbS, PbSe and PbTe; (2) indium compounds, such as InSb, InAs and InGaAs; (3) formulations of HgCdTe; and (4) platinum silicide (PtSi). Those skilled in the art are able to design an IR detector as a function of application specifics.

Multi-well plate 200, which comprises wells having an IR-reflective coating, has been previously described. For use in conjunction with IR imaging system 500B, multi-well plate 200 can comprise wells 106A, 106B or 106C.

In IR imaging system 500B depicted in FIG. 6, multi-well plate 200 and infrared detector 644 are disposed in parallel, opposed and aligned relation. "Opposed" means that surface 104 of multi-well plate 200 (see FIG. 2) faces IR receiving surface of infrared detector 644. "Aligned" means that specific groupings of sensor elements 646 overlie specific wells in multi-well plate 200.

In use, at least some of wells 106A, 106B or 106C of multi-well plate 200 contain reagents; those wells are being monitored by infrared detector 644 for the occurrence of target events. When exposed to infrared-spectrum radiation having a wavelength that is within its operating range, sensor elements 646 generate an electrical response that is read-out in well-known fashion. In this regard, focal plane arrays are similar to the well-known CCDs. Various configurations other than focal plane arrays, as are commercially available, may suitably be used. Focal plane arrays are commercially available from Sensors, Inc. of Princeton, N.J., among others.

The infrared radiation emitted from a particular well of multi-well plate 200 is received by only a small portion of the total of sensor elements 646 comprising detector 644. Consequently, multiple groups of sensor elements 646 are required to detect all of the target events that are occurring on multi-well plate 200. Before the detector is operated, each such group must therefore be assigned to detect the radiation being emitted from a given well of multi-well plate 200, in known fashion. Once established, this assignment of sensor elements 646 fixes the alignment of infrared detector 644 with respect to multi-well plate 200.

The electrical responses from sensor elements 646 are read-out and combined in known fashion to produce detector output signals $648_{i, i=1,n}$, which are delivered to signal processing electronics 650 for analysis. Signal processing electronics 650 include analog-to-digital converter 652 and data processing system 654. Analog-to-digital ("A/D") converter 652 converts analog signals $648_{i, i=1,n}$ to digital signals suitable for processing by data processing system 654.

Data processing system 654 comprises input/output ("I/O") 656, processor 658, and data storage device 660. I/O 656 includes machine interfaces (e.g., input and output ports, etc.) and human interfaces (e.g., keyboard, monitor, etc.). Data storage device 660 is advantageously a non-volatile memory. Processor 658 is advantageously capable of controlling the operation of IR detector 644, of receiving data from and outputting data to I/O 656, of storing data in and retrieving data from data storage device 660, and is further capable of executing programs, such as analysis software 662, that are stored in data storage device 660. Data processing should be fast enough and powerful enough to simultaneously monitor all wells.

In some variations, IR imaging system 500B includes positioner 664, which incorporates positioner drive 666 and drive linkage 668. Positioner 664 is used to move multi-well plate 200 between a first position, wherein it is underneath IR detector 644 as depicted in FIG. 6, to a second position, wherein multi-well plate 200 is not beneath IR detector 644. This allows multi-well plate 200 to be emptied and refilled, for example. In a variation of IR imaging system 500B depicted in FIG. 6, positioner 664 can suitably engage IR detector 644 for movement, rather than moving multi-well plate 200. Positioner 664 can be any one of a variety of mechanisms known in the art, such as, without limitation, a motorized linear positioning stage.

In IR imaging system 500B, the source of the emitted IR radiation (i.e., the target events that are occurring in wells 106A, 106B or 106C) is advantageously in the immediate proximity (defined in co-pending application PH1094) of the detector 644. In particular, in some embodiments, there is only a very small space S between multi-well plate 200 and IR detector 644. Space S is typically about 1 millimeter or less.

As previously described, hemispheric-shaped wells 106A and parabolic-shaped wells 106B and 106C have an IR reflective coating. And even though IR detector 644 is very close to multi-well plate 200, the performance of IR imaging system 500B still benefits from the IR reflective wells of multi-well plate 200.

In a particularly advantageous variation in accordance with the illustrative embodiment of the present invention, IR imaging system 500B includes multi-well plate 200 having parabolic-shaped wells 106B or 106C. As previously described, in IR imaging system 500B, a specific group of sensor elements 646 is "assigned" to image the IR radiation emitted from a specific well. As described in U.S. patent application No. 09/872,210, as space S between multi-well plate 200 and IR detector 644 increases, IR radiation emitted from a given well diverges such that, at some value of space S, radiation from the well "spills over" and is detected by the group of sensor elements that is assigned to detect the IR emissions from another well. As space S continues to increase, the ability to resolve the IR emissions from an individual well is lost.

In IR imaging system 500B, space S can be increased (compared to a similar system using conventional multi-well plates) since parabolic-shaped wells 106B or 106C are capable of increasing the amount of emitted IR that is directed along a path that is substantially normal to the mouth of the wells and, hence, substantially normal to IR detector 644. The ability to increase the size of space S in this fashion is expected to result in a greater number of acceptable configurations of the IR imaging system disclosed in U.S. patent application No. 09/872,210 (see description of $g_{min}$ and of $g_{max}$ as to limitations on allowable configurations).

Figure 7:
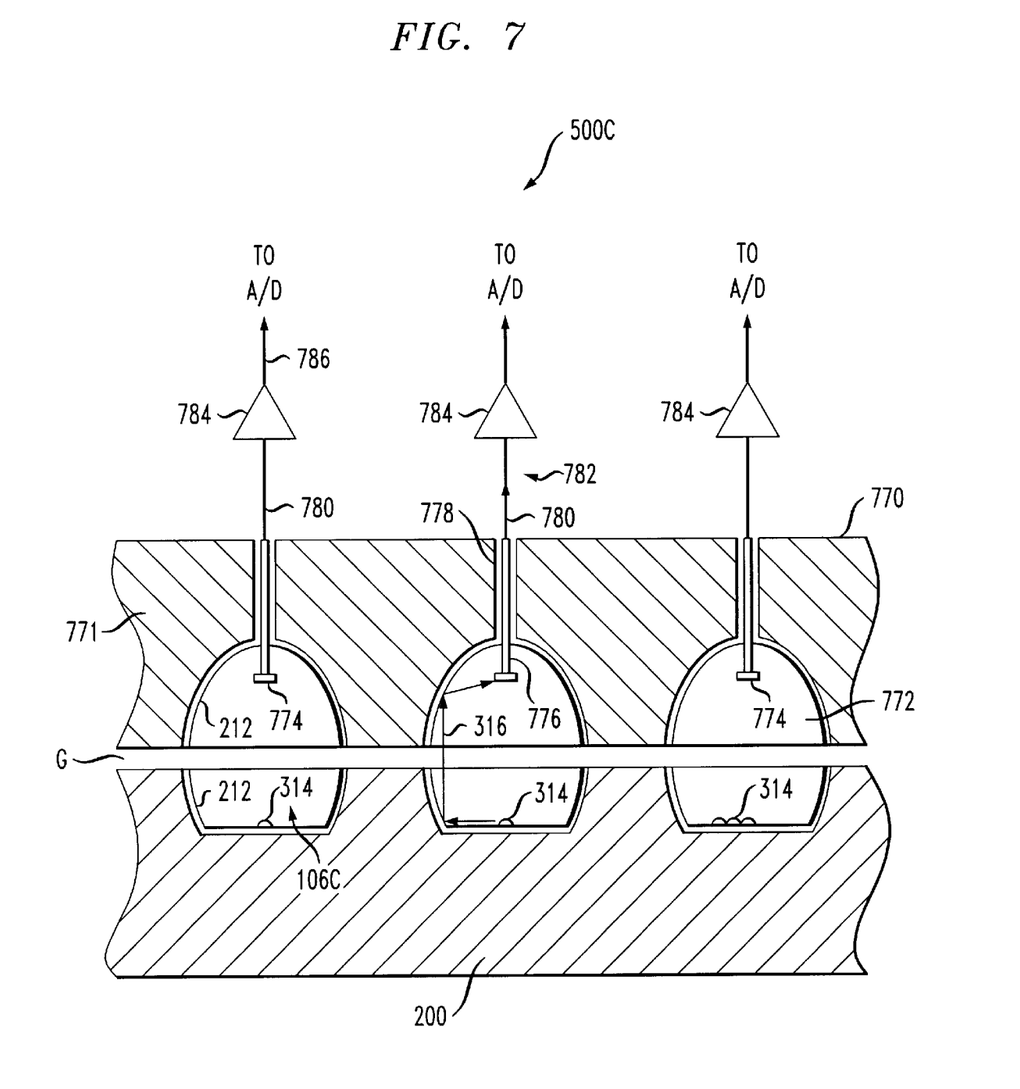
FIG. 7 depicts a third variation of an infrared imaging system in accordance with the illustrative embodiment of the present invention.

A third variation of an IR imaging system in accordance with the illustrative embodiment of the present invention is depicted in FIG. 7. IR imaging system 500C comprises two multi-well plates 200 and 770 that are in parallel, opposed and aligned relation with one another. In this context, the term "aligned" means that the wells from the opposed plates are aligned.

For its use in conjunction with imaging system 500C, multi-well plate 200, previously described, advantageously includes wells 106C, which have a parabolic or near-parabolic contour that is truncated near the focal plane. Since well 106C is truncated near the focal plane, reagents 314 within the well tend to be disposed near the focal point. Wells 106C include IR-reflective layer 212.

Multi-well plate 770, hereinafter "detector plate 770" has wells 772 that contain sensor elements 774 for sensing emitted IR, which is depicted as ray 316. Wells 772 of detector plate 770 have a parabolic or near-parabolic contour and, like wells 106C, include IR-reflective layer 212. When sensor elements 774 sense infrared radiation, they generate an electrical signal.

Sensor element 774 depends from support conduit 776 that extends through opening 778 in base 771. Sensor element 774 is positioned at the focal point of well 772. Sensor element 774 is electrically connected to externally located amplifier 784 by electrical conductor (e.g., wire, etc.) 780, which passes through support conduit 776. Each well 772 on detector plate 770 is paired (i.e., aligned) with one well 106C on multi-well plate 200. Among other benefits, this allows each sensor element 774 to be specifically selected for the IR emission wavelength of the target event occurring in the paired well 106C.

In operation, reagents 314 are added to wells 106C of multi-well plate 200. Typically, each target event being monitored involves at least two reagents; one of the reagents 314 varies (e.g., in concentration, identity, etc.) from well to well and the other does not. In some cases, some of the wells may be left empty or include a control (i.e., non-reactive substance). Liquid absorbs infrared radiation, and even a small amount of liquid can compromise the operation of infrared imaging systems described herein. Consequently, it is advantageous to provide the reagent that is varied in substantially solid form, such as in the form of a coating on a solid support.

Solid support media suitable for such service includes, without limitation, beads, pellets, disks, fibers, gels or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles or other material having a rigid or semi-rigid surface coated with hydrophobic polymer, etc., and soluble supports such as polyethylene glycol or low molecular weight non-cross-linked polystyrene. Advantageously, 200 micron PEG-grafted polystyrene beads (sold under the trademark "Tentagel™," by Rapp Polyether of Tubingen, Germany) are used as solid support media.

After the varying reagents 314 have been added, as desired, to wells 106C, the second non-varying reagent 314 is added to the wells. The second reagent is advantageously dispensed as an atomized or nebulized liquid that merely wets the first reagent. Dispensing the second reagent in this fashion avoids the aforementioned problem regarding IR absorption by liquid and, also, allows all wells to receive the second reagent substantially contemporaneously. A method and apparatus for dispensing such atomized/nebulized liquid is described in "Apparatus Comprising a Reagent Atomization and Delivery System," filed on Jun. 2, 2001 as U.S. patent application No. 09/872,415 and incorporated by reference herein.

A positioner (not depicted), is used to position multi-well plate 200 under detector plate 770 after reagents have been added to wells 106C and to move multi-well plate 200 away from detector plate 770 to prepare for a subsequent imaging run. The positioner, which can be configured to engage either multi-well plate 200 or detector plate 770 for movement, can be any one of a variety of mechanisms known in the art, such as, without limitation, a motorized linear positioning stage.

As a target event occurs, IR is emitted. To the extent that the source of the IR emission (e.g., reagent 314) is at or near the focal point of well 106C, emitted IR 316 that contacts IR reflective coating 212 is reflected therefrom substantially normal to the surface of multi-well plate 200. Emitted IR 316 then enters a paired well 772 of detector plate 770. Emitted IR 316 that contacts IR reflective coating 212 of well 772 is reflected therefrom to the focal point of well 772, which is where sensor element 774 is located.

When sensor element 774 receives emitted IR 316, it generates electrical signal 782 in known fashion. Signal 782 is conducted to amplifier 784 via electrical conductor 780. Amplified signal 786 is delivered to signal processing electronics (not depicted). Signal processing electronics typically includes an analog-to-digital ("A/D") converter and a data processing system. The A/D converter converts analog signal 786 to a digital signal that can be used by the data processing system. The data processing system usually comprises input/output ("I/O"), a processor and a data storage device. I/O includes machine interfaces (e.g., input and output ports, etc.) and human interfaces (e.g., keyboard, monitor, etc.). The data storage device is advantageously a non-volatile memory. The processor is advantageously capable of controlling the operation of IR imaging system 500C, of receiving data from and outputting data to I/O, of storing data in and retrieving data from the data storage device, and is further capable of executing programs, such as IR imaging software, that are stored in data storage device 660. Data processing should be fast enough and powerful enough to simultaneously monitor all wells.

Multi-well plate 200 and detector plate 770 are advantageously separated by gap G. The purpose for the gap is to prevent contamination of detector plate 770 by reagents from multi-well plate 200. Gap G is typically about 1 millimeter or less. In a variation of IR imaging device 500C, multi-well plate 200 abuts detector plate 770 such that there is no gap between these two plates. In such a variation, the contact surfaces of detector plate 770 and multi-well plate 200 should be wiped clean between imaging runs.

Figure 8:
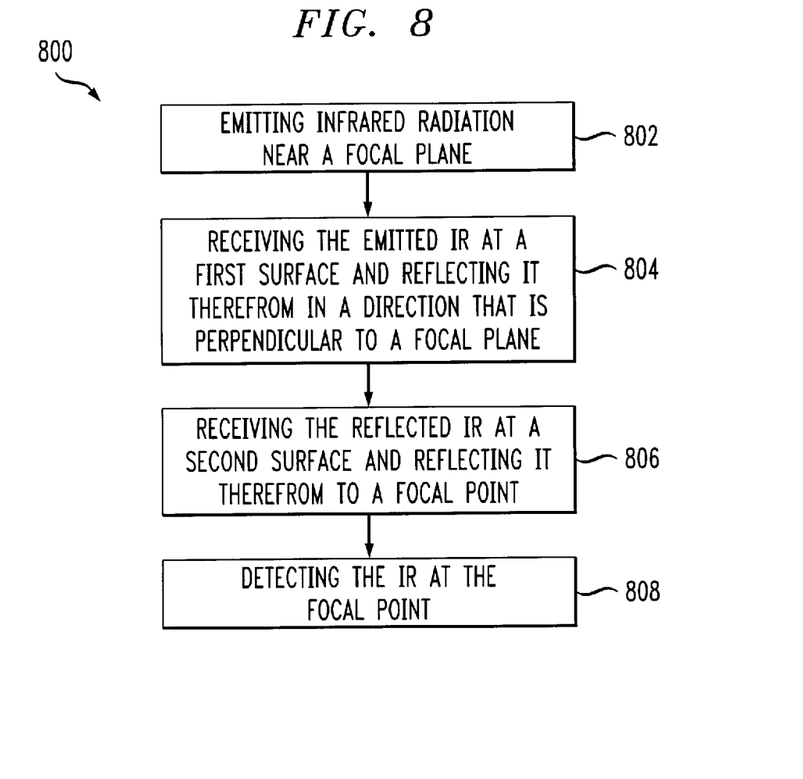
FIG. 8 depicts a method for imaging infrared radiation in accordance with the illustrative embodiment of the present invention.

FIG. 8 depicts a flow diagram of method 800 for imaging infrared radiation in accordance with the illustrative embodiment of the present invention. In accordance with operation 802 of method 800, infrared radiation is emitted near a focal plane. This is accomplished, for example, by placing reagents in wells 106C of micro-well plate 200. As previously described and depicted, wells 106C have a parabolic shape that is truncated at or near focal plane 1—1 (see FIGS. 4 and 7).

The emitted IR is received at a first surface and reflected from that surface in a direction that is normal to the focal plane, as per operation 804. This operation is accomplished, for example, by receiving the emitted IR at IR-reflective coating 212 (see FIG. 7). Since well 106C has a parabolic shape, IR radiation that is emitted at the focal point and is received by the IR-reflective coating 212 is reflected therefrom in a direction that is normal to the focal plane.

According to operation 806, the reflected IR is received at a second surface and is then reflected from that surface to a focal point. This operation is accomplished, for example, by having a second well that is disposed in opposed relation with well 106C, the second well having a parabolic shape and having an IR-reflective coating. This is depicted in FIG. 7, wherein (second) wells 772 of detector plate 770 face or oppose wells 106C of multi-well plate 200. Since wells 772 have a parabolic shape, IR ray 316 striking IR-reflective coating 212 of wells 772 in the normal direction is reflected to the focal point thereof.

As per operation 808, IR is detected at the focal point. This is can be accomplished by disposing, at the focal point, a sensor element (e.g., sensor element 774) that is operative to detect IR.

Figure 9:
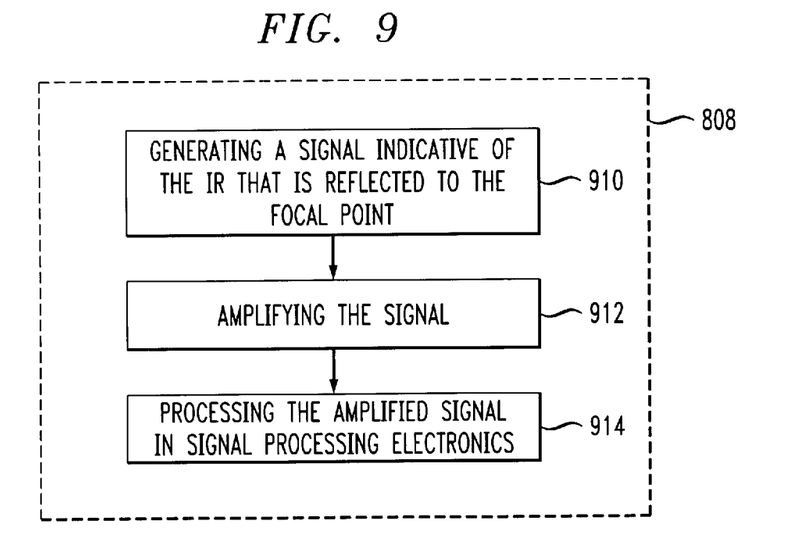
FIG. 9 depicts further steps in the method of FIG. 8.

In some variations, detecting IR at the focal point (i.e., operation 808) comprises several sub-operations, as shown in FIG. 9. In particular, operation 808 further includes operation 910 that comprises generating a signal that is indicative of the IR that is reflected to the focal point. In another variation of method 800, operation 808 includes operation 912 that comprises amplifying the generated signal. And, in yet a further variation of method 800, operation 808 includes operation 914 that comprises processing the amplified signal via signal processing electronics.

Figure 10:
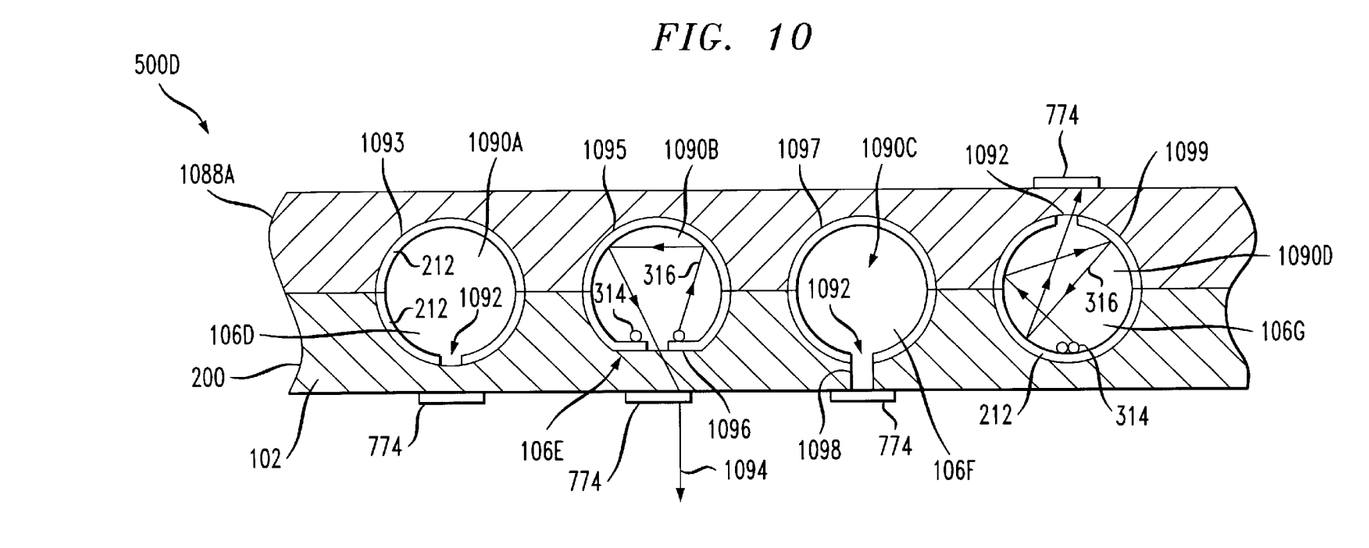
FIG. 10 depicts a fourth variation of an infrared imaging system in accordance with the illustrative embodiment of the present invention.

A fourth variation of IR imaging system in accordance with the illustrative embodiment of the present invention is depicted in FIG. 10. IR imaging system 500D comprises multi-well plate 200 and reflector 1088A that abut one another in opposed and aligned relation.

In the variation of IR imaging system 500D depicted in FIG. 10, each well from multi-well plate 200 has a hemispherical or truncated hemispherical shape and is coated with IR reflective coating 212. Similarly, in reflector 1088A, each well has a hemispherical shape and is coated with IR reflective coating 212. When plate 200 and reflector 1088A are brought together, wells aligned, each pair of aligned wells forms a substantially spherical enclosure 1090A–1090D (collectively, spherical enclosure 1090). Each spherical enclosure 1090 is provided with radiation-transparent window 1092, through which IR passes.

Infrared radiation 316 that is emitted (i.e., by reagents 314) escapes spherical enclosure 1090 only through radiation-transparent window 1092. IR 316 passing through radiation-transparent window 1092 is directly received by or conducted to sensor element 774, which generates electrical signal 1094 that is indicative of the intensity of the IR that it receives. Signal 1094 is processed (e.g., amplified, digitized, etc.) in the manner previously described.

For IR imaging system 500C (previously described) having parabolic-shaped wells, maximum sensitivity is provided when reagent is disposed at the focal point of the well 106C and sensor element 774 is disposed at the focal point of paired well 772. But in IR imaging system 500D, wherein sensor element 774 is disposed outside the paired wells and receives IR through a radiation-transparent window, hemispheric-shaped wells are advantageously used to provide a spherical shaped enclosure when mated.

Spherical enclosures 1090, and the wells that form them, can have any one of several configurations, a few of which are illustrated in FIG. 10 and described below. It will be understood that the illustrative configurations are depicted together in FIG. 10 for convenience; in actual practice, the enclosures within a given IR imaging system 500D are uniform (i.e., have a single configuration).

Spherical enclosure 1090A comprises well 106D from multi-well plate 200 and well 1093 from reflector 1088A. Well 1093 has a hemispherical shape and is fully coated with IR reflective layer 212. Well 106D has a hemispherical shape and is coated with IR reflective layer 212 except for a small region at the bottom of the well, at which the coating is absent. The coating-free region forms radiation-transparent window 1092. In this variation, base 102 must be transparent to IR at the emission wavelengths so that IR escaping through radiation-transparent window 1092 can pass through base 102 to sensor element 774.

Spherical enclosure 1090B comprises well 106E from multi-well plate 200 and well 1095 from reflector 1088A. Well 1095 has a hemispherical shape and is fully coated with IR reflective layer 212. The hemispheric shape of well 106E is truncated such that the well has flat bottom 1096. Like well 106D, well 106E is coated with IR reflective layer 212 except for a small region at the bottom of the well. The non-coated region of well 106E forms radiation-transparent window 1092. Base 102 must be transparent to IR at the emission wavelengths.

Spherical enclosure 1090C comprises well 106F from multi-well plate 200 and well 1097 from reflector 1088A. Well 1097 has a hemispherical shape and is fully coated with IR reflective layer 212. Well 106F provides an example of a configuration that is used when base 102 of multi-well plate 200 is opaque to IR at the emission wavelengths. In particular, like wells 106D and 106E, hemispheric-shaped well 106F is coated with IR reflective layer 212 except for a small region at the bottom of the well. But unlike the other variations, the portion of base 102 located beneath radiation-transparent window 1092 of enclosure 1090C is removed to allow IR escaping from the radiation-transparent window to reach sensor element 774. Thus, in FIG. 10, hole 1098 leads from the bottom of well 106F completely through the remainder of base 102. For use in conjunction with a well in multi-well plate 200, such as well 106F, hole 1098 is advantageously filled with an IR transparent material, such as quartz, germanium, etc, to prevent contamination of sensor element 774. In one variation (not shown), radiation-transparent window 1092 and hole 1098 are associated with well 1097 in reflector 1088A, and sensor element 774 is located on the upper surface of reflector 1088A. With this configuration, hole 1098 need not be filled to prevent contamination of sensor element 774.

In a further variation of IR imaging system 500D, spherical enclosure 1090D comprises well 106G from multi-well plate 200 and well 1099 from reflector 1088A. Well 106G has a hemispheric-shape and is fully coated with IR reflective layer 212. In this variation, it is paired well 1099 from reflector 1088A that has a small non-coated region that defines radiation-transparent window 1092.

Figure 11:
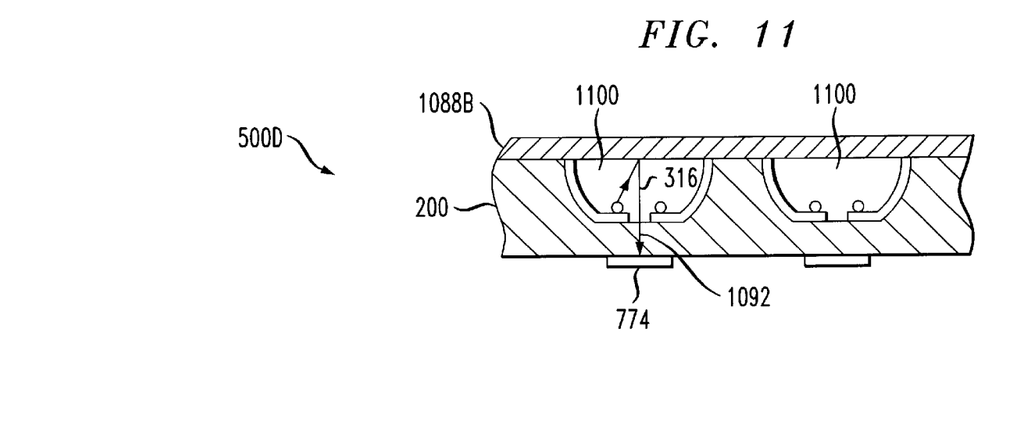
FIG. 11 depicts a further variation of the infrared imaging system depicted in FIG. 10.

FIG. 11 depicts a further a variation of IR imaging system 500D wherein the reflector (i.e., reflector 1088B) is a flat IR reflective surface, such as a slide, etc., that is coated with gold, polished copper, etc. Enclosure 1100 is hemispherical, not spherical, in variations wherein IR imaging system includes flat reflector 1088B. Yet, enclosure 1100 functions in the same manner as spherical enclosure 1090. That is, reflector 1088B is capable of reflecting substantially all IR 316 that it receives back to multi-well plate 200. Consequently, like spherical enclosure 1090, IR 316 escapes from enclosure 1100 only a through radiation-transparent window 1092.

In operation, reagents 314 are added to wells 106D, 106E, 106F or 106G (hereinafter collectively wells 106) of multi-well plate 200. Reflector 1088A, 1088B (hereinafter collectively "reflector 1088") and plate 200 must be separated to allow access to the wells of plate 200 for this purpose. In some variations, plate 200 is attached to reflector 1088, such as by a hinge (not shown). A robotic arm is advantageously used to rotate reflector 1088 about the hinge for emptying and refilling the wells. Of course, reflector 1088 can be moved manually.

In some variations of IR imaging system 500D in which reflector 1088 and multi-well plate 200 are not hinged or otherwise attached to one another, a positioner (not shown) is advantageously used to move reflector 1088 away from and into position on multi-well plate 200. Alternatively, the positioner can move multi-well plate 200 rather than reflector 1088. In preferred embodiments, the actuated member (i.e., multi-well plate 200 or reflector 1088) is the one that does not include radiation-transparent windows 1092. The positioner can be any one of a variety of mechanisms known in the art, such as, without limitation, a motorized linear positioning stage.

As previously described, each target event being monitored typically involves at least two reagents; one of the reagents 314 varies (e.g., in concentration, identity, etc.) from well to well, while the other does not. It is advantageous to provide the reagent that is varied in substantially solid form, such as in the form of a coating on a solid support.

After varying reagents 314 have been added, as desired, to wells 106, the second reagent is added to the wells. As previously described, the second reagent, which typically does not vary from well to well, is advantageously dispensed as an atomized or nebulized liquid that merely wets the first reagent. Once the second reagent is dispensed, multi-well plate 200 and reflector 1088 are brought together forming spherical enclosure 1090 (FIG. 10) or hemispherical enclosure 1100 (FIG. 11). Emitted IR 316 is reflected with the enclosure until it escapes through radiation-transparent window 1092.

FIGS. 10 and 11 depict sensor elements 774 abutting the lower surface of multi-well plate 200. While shown as individual sensor elements in those Figures, sensor elements 774 are advantageously part of a sensor array (e.g., a focal plane array, etc.). And since there is no opportunity for contamination of sensor elements 774, multi-well plate 200 can be disposed directly on the sensor array.

This configuration (i.e., multi-well plate 200 abutting sensor array) might be inappropriate for any number of reasons, such as, for example, when multi-well plates having a large number of very small wells are used. In such a case, polycrystalline IR fibers, such as are available from ART-PHOTONICS, GMBH, Berlin, Germany, are used to conduct IR from radiation-transparent window 1092 to remote sensor elements 774, as depicted via a perspective view in FIG. 12.

Figure 12:
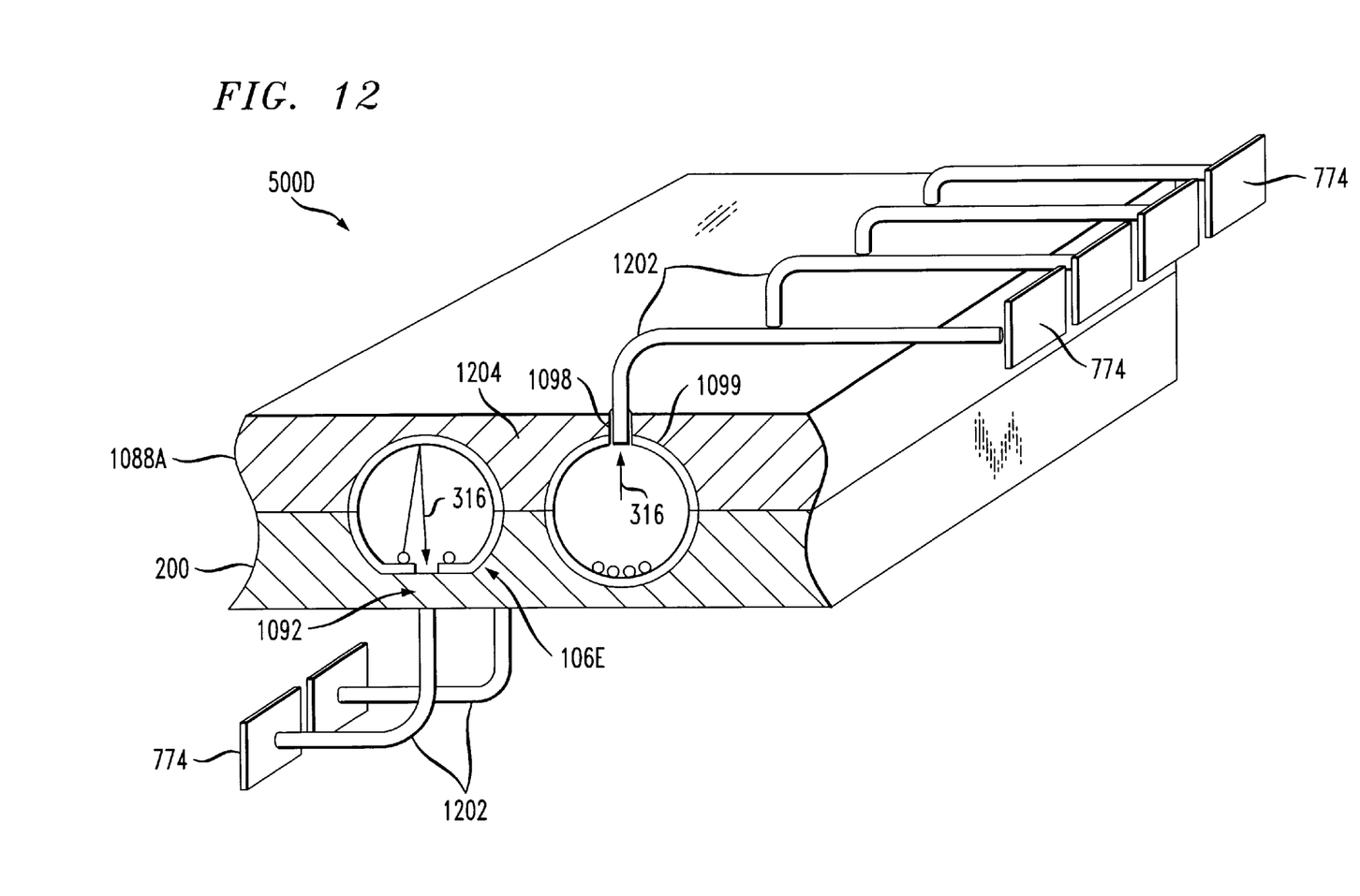
FIG. 12 depicts an additional variation of the infrared imaging system depicted in FIG. 10 wherein IR-reflective fibers are used to conduct infrared radiation from a well to a detector.

FIG. 12 depicts two variations of spherical enclosure 1090. In one, IR 316 escapes to fibers 1202 through radiation-transparent window 1092 of truncated hemispherical well 106E in multi-well plate 200. Fibers 1202 conduct the IR to sensors 774. In another variation, IR 316 escapes to fibers 1202 through radiation-transparent window 1092 of hemispherical well 1099 of reflector 1088A. In this variation, hole 1098, which leads from well 1099 through base 1204 of reflector 1088A, receives an end of fiber 1202. In variations in which fiber 1202 is inserted into hole 1098, the hole and radiation-transparent window 1092 are advantageously disposed in reflector 1088A. Otherwise, the fiber would be regularly contaminated (if it abutted the well containing the reagents).

It is to be understood that the above-described embodiments are merely illustrative of the invention and that many variations may be devised by those skilled in the art without departing from the scope of the invention and from the principles disclosed herein. It is therefore intended that such variations be included within the scope of the following claims and their equivalents.

I claim:

1. An article comprising an infrared imaging system, said infrared imaging system comprising:
   a multi-well plate, wherein said multi-well plate comprises:
      a base comprising a first material;
      a plurality of wells disposed in said base, said wells having a mouth that is substantially co-planar with a first major surface of said base; and
      a coating disposed on said wells, said coating comprising a second material that reflects infrared radiation; and
   a detector plate, wherein said detector plate is disposed in parallel, opposed and aligned relation with said multi-well plate, wherein said detector plate comprises:
      a plurality of wells having a parabolic shape;
      a coating disposed on said wells, said coating comprising a third material that reflects infrared radiation; and
      a sensor element disposed at a focal point within said wells, wherein said sensor element generates a signal indicative of infrared radiation it receives.

2. The article of claim 1 wherein a number of wells in said detector plate is equal to a number of wells in said multi-well plate.

3. The article of claim 2 wherein said number of wells is selected from the group consisting of 96 wells, 384 wells and 1536 wells.

4. The article of claim 1 wherein said detector plate further comprises a base, wherein said wells are disposed in said base, said base comprising:
   a first major surface that is co-planar with a mouth of said wells;
   a second major surface that is parallel to said first major surface; and
   openings through said base that place an interior of said wells in communication with said second major surface.

5. The article of claim 4 further comprising a plurality of support conduits, wherein:
   one of said support conduits is disposed within each said opening through said base;
   a first end of said support conduit extends into said well; and
   said sensor element is attached to said first end of said support conduit.

6. The article of claim 5 further comprising an electrical conductor that is electrically connected to each said sensor element, wherein a portion of said electrical conductor is disposed within said support conduit.

7. The article of claim 6 wherein said electrical conductor is also electrically connected to an amplifier.

8. The article of claim 1 further comprising a space that separates said detector plate from said multi-well plate.

9. The article of claim 8 wherein said space is about 1 millimeter.

10. An article comprising an infrared imaging system, said infrared imaging system comprising:
   a multi-well plate, wherein said multi-well plates comprises:

a base comprising a first material;

a plurality of wells disposed in said base, said wells having a mouth that is substantially co-planar with a first major surface of said base; and a coating disposed on said wells, said coating comprising a second material that reflects infrared radiation; and wherein said wells have a hemispheric shape and each said well has a radiation-transparent window that is transparent to infrared radiation; and further comprising:

a reflector that is in optical communication with said mouth of each said well, wherein said reflector reflects substantially all infrared radiation leaving said mouth of said wells back into said wells; and a sensor element that is in optical communication with said radiation-transparent window, wherein said sensor element generates a signal indicative of infrared radiation that it receives.

11. The article of claim 10 wherein said hemispheric shaped-wells are truncated such that the bottom of said wells are flat.

12. The article of claim 11 wherein said reflector comprises:

a plurality of wells having a hemispheric shape; and a IR-reflective coating that is disposed on said wells.

13. The article of claim 11 wherein said reflector is hingeably attached to said multi-well plate.

14. The article of claim 11 further comprising a fiber, a first end of which fiber is in optical communication with said radiation-transparent window and a second end of which fiber is in optical communication with said sensor element.

15. An article comprising:

a base comprising a material having a low thermal conductivity;

a plurality of wells having a parabolic shape and disposed in a two-dimensional array at a first major surface of said base, a coating disposed on said wells, said coating comprising a material that reflects infrared radiation; and a sensor element disposed at a focal point within said wells, wherein said sensor element generates a signal indicative of infrared radiation that it receives.

16. The article of claim 15 further comprising an electrical conductor that is electrically connected to said sensor element and that conducts said signal out of said well.

17. The article of claim 15 wherein said wells are truncated at or near a focal plane.

18. An article comprising:

a multi-well plate, wherein said multi-well plate comprises:

a base comprising a material having a low thermal conductivity;

a first plurality of wells having a hemispheric shape and disposed in a two-dimensional array at a first major surface of said base, a first coating disposed on said first plurality of wells, said first coating comprising a material that reflects infrared radiation;

a reflector, wherein said reflector comprises:

a second plurality of wells each having a hemispheric shape;

a second coating disposed on said second plurality of wells, said second coating comprising a material that reflects radiation;

and wherein:

said reflector and said multi-well plate are disposed in abutting relation; and each well of said reflector aligns with one well of said multi well plates forming a plurality of closed, substantially spherical enclosures;

a plurality of windows, wherein:

said windows are transparent to infrared radiation; and each said substantially spherical enclosure has one said window;

and a sensor element, wherein:

said sensor element is in optical communication with said window;

and said sensor element generates a signal indicative of infrared radiation that it receives.

19. The article of claim 18 wherein said hemispheric shaped-wells in said multi-well plate are truncated such that the bottom of said wells are flat.

20. The article of claim 19 wherein one of said windows is disposed in each well in said multi-well plate.

21. The article of claim 18 wherein one of said windows is disposed in each well in said reflector.

22. The article of claim 18 wherein said window is selected from the group consisting of polypropylene, quartz and germanium.

23. A method comprising:

emitting infrared radiation near a focal plane;

receiving said emitted infrared radiation at a first surface;

reflecting said received infrared radiation from said first surface in a direction that is perpendicular to said focal plane;

receiving said reflected infrared radiation at a second surface;

reflecting said received, reflected infrared radiation from said second surface to a focal point; and detecting said infrared radiation at said focal point.

24. The method of claim 23 wherein the step of detecting further comprises generating a signal indicative of the infrared radiation that is reflected to said focal point.

25. The method of claim 24 wherein said step of detecting further comprises amplifying said signal.

26. The method of claim 25 wherein said step of detecting further comprises processing the amplified signal in signal processing electronics.

* * * * *